US006923956B1

United States Patent
Tschope et al.

(10) Patent No.: US 6,923,956 B1
(45) Date of Patent: Aug. 2, 2005

(54) LIQUID INTERFERON-β FORMULATIONS

(75) Inventors: Michael Tschope, Sibecrach (DE);
Thomas Siklosi, Walpertshofen (DE);
Peter Schroeder, Laupheim (DE);
Hans Hofer, Walpertshofen (DE)

(73) Assignee: Rentschler Biotechnologie GmbH,
Laupheim (DE)

( * ) Notice: Subject to any disclaimer, the term of this patent is extended or adjusted under 35 U.S.C. 154(b) by 0 days.

(21) Appl. No.: 09/508,510

(22) PCT Filed: Sep. 23, 1998

(86) PCT No.: PCT/EP98/06065
§ 371 (c)(1),
(2), (4) Date: May 26, 2000

(87) PCT Pub. No.: WO99/15193
PCT Pub. Date: Apr. 1, 1999

(30) Foreign Application Priority Data

Sep. 23, 1997 (EP) .............................. 97116562

(51) Int. Cl.⁷ .................. A61K 38/21; A61K 38/00;
A61K 38/28; A61K 38/16; C07K 17/00
(52) U.S. Cl. .............................. 424/85.6; 514/2; 514/4;
514/8; 530/351
(58) Field of Search .................. 424/85.7; 514/2, 514/4, 8; 530/351

(56) References Cited

U.S. PATENT DOCUMENTS 5,151,265 A  *  9/1992  Hwang-Felgner et al. . 424/85.5
5,358,708 A     10/1994  Patel ......................... 424/85.1

FOREIGN PATENT DOCUMENTS

| EP | 0 284 249 A1 | 9/1988 |
| EP | 0 374 257 | 6/1990 |
| EP | 0 529 300 | 3/1993 |
| WO | WO89/02750 A1 | 4/1989 |
| WO | WO92/15614 A1 | 9/1992 |
| WO | 98 28007 | 7/1998 |

OTHER PUBLICATIONS

Abstract/Figure, EMBL Research Reports, Table of Contents (1 page) 2001.

"Opposition of Bioceuticals Arzneimittel AG" to EP APN 98950074.9: Jul. 4, 2003; Jul. 31, 2003.

"Opposition of Intellectual Property Services" to EP APN 98950074.9: Jul. 4, 2003; Jul. 10, 2003.

* cited by examiner

*Primary Examiner*—Janet Andres
(74) *Attorney, Agent, or Firm*—Rothwell Figg Ernst & Manbeck

(57) ABSTRACT

The present invention relates to liquid formulations of human interferon-β. The formulations are characterized in that they have a buffer with a pH in the weakly acidic to neutral range of between 5 and 8, preferably between over 5.5 and 8, and that they exhibit high stability of the interferon-β in solution while retaining the molecular integrity.

19 Claims, No Drawings

LIQUID INTERFERON-β FORMULATIONS

CROSS REFERENCES TO RELATED APPLICATIONS

This application is a § 371 of PCT/EP98/06065, filed on Sep. 23, 1998.

BACKGROUND OF THE INVENTION

1. Field of the Invention

The present invention relates to liquid formulations of human interferon-β. The formulations are characterized in that they have a pH in the weakly acidic to neutral range between 5 and 8 and that the interferon-β is highly stable in solution while retaining the molecular integrity.

2. Description of Related Art

Naturally occurring interferons are species-specific proteins, in some cases glycoproteins, which are produced by various cells of the body after induction with viruses, double-stranded RNA, other polynucleotides and antigens. Interferons exhibit a large number of biological activities such as, for example, antiviral, antiproliferative and immunomodulatory properties. At least 3 different types of human interferons have been identified; they are produced by leucocytes, lymphocytes, fibroblasts and cells of the immune system and termed α-, β- and γ-interferons. Individual types of interferons can furthermore be divided into a large number of subtypes.

Native, human interferon-β can be prepared commercially by superinduction of human fibroblast cell cultures with poly-IC followed by isolation and purification of the interferon-β by chromatographic and electrophoretic techniques. Proteins or polypeptides which exhibit properties similar to those of natural interferon-β can also be prepared by recombinant DNA technologies (EP-A-0 028 033; EP-A-0 041 313; EP-A-0 070 906; EP-A-0 287 075; Chernajovsky et al. (1984) DNA 3, 297–308; McCormick et al. (1984) Mol. Cell. Biol. 4 166–172). Recombinant human interferon-β can be produced both in eukaryotic cells (for example CHO cells) and by prokaryotic cells (for example *E. coli*)

The interferons in question are termed interferon-β-1a and interferon-β 1b respectively. In contrast to interferon-β 1b, interferon-β 1a is glycosylated (Goodkin (1994) Lancet 344, 1057–1060).

A prerequisite for the therapeutic use of interferon-β is that it is pharmaceutically formulated so that the protein is storage-stable over a prolonged period while retaining the molecular integrity. Interferon-β is unstable and subject to various degradation reactions. These include, in particular, the cleavage of peptide bonds, deamidation, oxidation of the methionin to methionin sulphide, disulphide exchange, and changes in the sugar side chain which even include deglycosylation.

Owing to the therapeutic benefit of interferons, a series of formulations have been developed in recent years; however, all of them exhibit certain disadvantages. U.S. Pat. No. 4,647,454 (Inter-Yeda Ltd.) describes a formulation of fibroblast interferon-β which can be stabilized by addition of polyvinylpyrrolidone (PVP) in the highly acidic range (pH 3.5). Other preferred auxiliaries are mannitol, human serum albumin and acetate buffers. The formulation is freeze-dried and stored at 4° C.

The Japanese Patent Specification 59 181 224 (Sumitomo Chemical Co.) describes an aqueous solution of interferons in which polar amino acids such as arginine, asparagine, glutamic acid, glutamine, histidine, lysine, serine and threonine and their sodium salts together with human serum albumin are employed for stabilizing the interferons.

The international Patent Application WO 95/31213 (Applied Research Systems ARS Holding) describes a liquid formulation for interferon-β which is stabilized by addition of a polyol, preferably mannitol, and a non-reducing sugar or an amino acid. The formulation furthermore comprises a buffer (acetate buffer pH 3.0 to 4.0) and human serum albumin. While formulas with a pH of between 5 and 6 showed an immediate loss in biological activity, the formulas preferred in the patent specification are sufficiently stable at pH values of 3.0 and 4.0. Moreover, the statement regarding stability only refers to the biological activity of the formulation, but not to the molecular integrity of the active ingredient.

The European Patent Application EP 0 215 658 (Cetus Corp.) describes a formulation for recombinant interferon-β in which the bioactive compound is dissolved in an aqueous medium at a pH of between 2 and 4 with addition of stabilizers such as human serum albumin or human plasma protein fractions and, if appropriate, dextrose. A further patent application of Cetus Corp. (WO 89/05 158) describes a formulation for interferon-β where either glycerin or polyethylene glycopolymers with a mean molecular weight of between 190 to [sic] 1600 daltons are employed as stabilizers at a pH of between 2 and 4. Suitable buffer components which are mentioned are glycine, phosphoric acid and citric acid.

The European Patent Application EP 0 217 645 (Cetus Corp.) describes pharmaceutical preparations with IL-2 or interferon-β which are dissolved in an excipient medium at pH 7 to 8 and stabilized with addition of sodium laurate as surfactant. In addition, SDS is also required as further ionic surfactant in order to stabilize these preparations.

The European Patent EP 0 270 799 (Cetus Oncology Corp.) describes a formulation for unglycosylated recombinant interferon-β in an inert water-based excipient medium which comprises non-ionic polymeric detergents as stabilizer.

The European Patent Application EP 0 529 300 (Rentschler Biotechnologie GmbH) describes liquid interferon-β formulations which comprise a concentration of 30 or 70 MU/ml recombinant IFN-β, sodium chloride and imidazole buffer or sodium phosphate buffer and have a pH of 7.5 (Example 3). These formulations are stable with regard to their biological activity for 4 weeks at a storage temperature of 25° C. However, the disadvantage of these compositions is that the concentration of interferon-β used ($\geq 30$ MU/ml) is too high for practical applications. Moreover, there is no mention in EP-A-0 529 300 of a reduction in the stability of liquid interferon-β formulations by addition of human serum albumin. In contrast, the addition of human serum albumin is stated as being preferred.

In addition to formulations for interferon-β, there are also described pharmaceutical dosage forms with interferon-α. The European Patent Specification 0 082 481 (Schering Corp.) discloses an aqueous formulation intended for freeze-drying which comprises human serum albumin, in addition to a phosphate buffer and glycine. Alanine is mentioned as further optional constituent. After reconstitution, the pH of the solution is between 7.0 and 7.4. A further patent application of Schering Corp. (WO 96/11018) discloses stable aqueous solutions in interferon-α which comprise chelating agents (NaEDTA or citric acid), a surfactant (Polysorbat 80), an isotonizing agent (sodium chloride) and suitable preservatives such as methylparaben, propylparaben, m-cresol or phenol, at a pH of between 4.5 and 7.1. With regard to the biological activity (standard method of inhibiting the cytopathic effect (CPE) of a virus as described by W. P. Protzman in J. Clinical Microbiology, 1985, 22, pp. 596–599), the aqueous formulations disclosed prove to be stable for 6 months at 25° C. (biological activity >90% of the initial activity). However, a determination of the protein content by HPLC carried out in parallel already shows losses in content of between 20.2 (Table 3) or 32.5% (Table 4) after 6 months at 25° C.

EP-A-0 736 303 (Hoffmann-LaRoche AG) discloses aqueous interferon-$\alpha$ compositions which, in addition to an interferon-$\alpha$, comprise a non-ionic detergent, a buffer for setting the pH range between 4.5 and 5.5, benzyl alcohol and, if appropriate, isotonizing agents. A determination by HPLC identifies a residual content of 84.5% after storage for three months at 25° C. and a starting concentration of 18 MU interferon-$\alpha$2a, while this value drops to 62.8% when the stabilizer benzyl alcohol is omitted.

EP-A-0 641 567 (Ciba Geigy AG) describes pharmaceutical compositions which comprise hybrid interferon-$\alpha$ and, as stabilizer, a buffer with a pH of between 3.0 and 5.0.

U.S. Pat. No. 5,358,708 (Schering Corp.) describes aqueous formulations of interferon-$\alpha$ which comprise methionine, histidine or mixtures of these as stabilizer. After storage of an interferon-$\alpha$ solution at 40° C. for two weeks, it is found that the active ingredient content has decreased by 20%.

The abovementioned formulations for interferons have shortcomings from the present-day view since, for example, an addition of human serum albumin for stabilizing proteins should be dispensed with, owing to the higher demands for safety from virus contamination by blood donors. Moreover, a number of the above-described formulations require the addition of amino acids and/or freeze-drying. However, freeze-dried products are complicated to produce and, accordingly, expensive and require an additional pass owing to the necessity of reconstitution, and this additional pass is frequently very difficult to perform, in particular for patients with a limited power of movement. A series of formulas have unphysiological pH values of below 5.0. While such values are not entirely unusual (see also S. Sweetana and N. J. Aders, Journal of Pharmaceutical Sciences and Technology, 1996, 50: 330–342), painful irritation must be expected in the case of intramuscular or subcutaneous application. While according to Sweetana and Akers the use of surfactants such as Polysorbat 80 is admissible, a series of side effects have been described, in particular in new-born and older children, which make the use of such auxiliaries questionable. A review of the toxicity of surfactants can be found in Attwood and Florence (Surfactant Systems, their Chemistry, Pharmacy and Biology, Chapman and Hall; London, 1983). The pharmacology of Polysorbat 80 is reviewed by R. K. Varma et al. (Arzneim.-Forsch./Drug Res. 35, 1985, 804–808).

On the basis of the abovementioned disadvantages, an optimal formulation for interferon-$\beta$ should combine the following properties:

retaining the biological activity over the storage period, retaining the molecular integrity of the active ingredient molecule over the storage period, liquid formulation, no expensive freeze-drying and no additional reconstitution, no risky auxiliaries such as human serum albumin or surfactants (detergents), pH in the neutral to weakly acidic range.

BRIEF SUMMARY OF INVENTION

A first aspect of the present invention is therefore a liquid pharmaceutical formulation which comprises human interferon-$\beta$ as active ingredient in a concentration of up to 25 MU/ml and a buffer for setting a pH of between 5 and 8, preferably between over 5.5 and 8, is free from human serum albumin and shows a long-term stability of the biological activity (in vitro) of at least 80% of the initial activity after storage for 3 months at 25° C.

A further aspect of the invention is a liquid pharmaceutical formulation which comprises human interferon-$\beta$ as active ingredient and a buffer for setting a pH of between 6 and 7.2, is free from human serum albumin and shows a long-term stability of the biological activity (in vitro) of at least 80% of the initial activity after storage for 3 months at 25° C.

Yet a further aspect of the invention is a liquid pharmaceutical formulation which comprises human IFN-$\beta$ as active ingredient, a buffer for setting a pH of between 5 and 8, preferably between over 5.5 and 8, and one or more amino acids and shows a long-term stability of the biological activity (in vitro) of at least 80% of the initial activity after storage for 3 months at 25° C.

All requirements are met by the invention, which is described in greater detail in the section which follows.

DETAILED DESCRIPTION OF INVENTION

Surprisingly, a composition of a formula has been found which ensures the molecular integrity of interferon-$\beta$ in liquid form over a prolonged period in a physiological pH range of between 5 and 8, preferably between over 5.5 and 8, without having to resort to the auxiliaries of the prior art, which are known as being disadvantageous.

The long-term stability of liquid pharmaceutical formulations was measured at 25° C. The temperature of 25° C. was chosen, on the one hand, to cause accelerated degradation reactions, but, on the other hand, to avoid artefacts caused by unduly high temperatures. Suitable analytical methods for determining the stability of interferon-$\beta$ can be found in the reviews by J. Geigert (J. Parent. Sci. Technol. 43 (1989), 220–224) or M. C. Manning, K. Patel and R. T. Borchardt (Pharm. Res. 6 (1989), 903–918).

The biological activity after the storage period chosen in each case was measured by the standard method of inhibiting the cytopathic effect of a virus. A detailed description of the test method used can be found in Stewart, W. E. II (1981): The Interferon System (Second, enlarged Edition), Springer-Verlag: Vienna, N.Y.; Grossberg, S. E. et al. (1984), Assay of Interferons. In: Came, P. E., Carter W. A (eds) Interferons and their Applications, Springer-Verlag: Berlin, Heidelberg, N.Y., Tokyo, pp. 23–43. After storage for three months at 25° C., a formulation according to the invention exhibits a biological activity of at least 80%, preferably of at least 85%, and especially preferably of at least 90%, of the initial activity.

After storage for six months at 25° C., a formulation according to the invention preferably has a biological activity of at least 80%, and preferably of at least 85%, of the initial activity.

Even when stored at higher temperatures, for example 37° C., the formulations according to the invention exhibit a surprisingly high long-term stability of the biological activity. For example after storage for one month at 37° C., a biological activity of at least 70%, and preferably of at least 80%, of the initial activity is found.

The liquid pharmaceutical formulations according to the invention are preferably free from human serum albumin and especially preferably—apart from the active ingredient—free from human or animal polypeptides, in particular serum proteins. It is furthermore preferred for the liquid pharmaceutical formulation according to the invention to be free from surfactants, in particular free from ionic detergents and/or non-ionic surfactants.

The formulations according to the invention comprise, S as active ingredient, an interferon-β, that is to say a polypeptide which exhibits biological and/or immunological properties of natural human interferon-β and which may be a naturally occurring or recombinant interferonon-β. The formulation preferably comprises a glycosylated interferon-β, especially preferably a recombinant interferon-β from CHO cells. Interferonon-β species which are most preferably used are those which can be obtained from the cell line BIC 8622 (ECACC 87 04 03 01) and which are described, for example, in EP-B-0 287 075 and EP-A-0 529 300.

Preferably, the active ingredient is present in the formulations according to the invention in a concentration of up to 25 MU/ml. However, a dosage in the range of 1 to 25 MU/ml is preferred, in the range of 3 to 20 MU/ml especially preferred and in the range of 3 to 10 MU/ml most preferred. These dosage ranges allow an immediate use without further dilution in conjunction with a particularly good stability at an elevated temperature.

A further preferred feature of the liquid pharmaceutical formulation according to the invention is that it exhibits a chemical integrity after storage for 3 months, and preferably 6 months, at 25° C., i.e. that it is stable to peptide cleavage, oxidation and deglycosylation. The chemical integrity is measured by peptide mapping, Western blot and glycosylation analysis. Chemically stable for the purposes of the present invention are compositions in which the interferon-β after formulation retains at least 85%, preferably at least 90%, of the chemical integrity at the storage conditions chosen.

A further preferred feature of the liquid pharmaceutical formulations according to the invention is a physical integrity after storage for 3 months, and preferably 6 months, at 25° C. The physical integrity is in this case measured by measuring the transmission at 420 nm and by visually observing the solutions. Physically stable are those solutions whose transmission is over 90%, preferably over 93%, at the storage conditions chosen, and where no turbidity can be determined upon visual observation.

The present invention surprisingly allows liquid formulations of interferon-β to be provided which are biologically, chemically and physically stable over a prolonged period and free from undesired constituents such as, for example, human serum albumin or surfactants. In addition to the active ingredient, the formulations according to the invention comprise a buffer which is preferably present in a concentration of 10 mmol/l to 1 mol/l, especially preferably in a concentration of 20 mmol/l to 200 mmol/l, for example approximately 50 mmol/l to 100 mmol/l, and which serves to maintain the pH of the formulation in the range of 5 to 8, preferably above 5.5 to 8, more preferably between 6 and 7.4. A pH range between 6 and 7.2 is especially preferred, and a pH range between 6.2 and 6.8 most preferred, since a particularly high stability while retaining the molecular integrity is achieved here. The buffer is selected from amongst pharmaceutically acceptable buffers, for example borate, succinate, L-malate, TRIS, salicylate, glycylglycine, triethanolamine, isocitrate, maleate, phosphate, citrate and acetate buffer, or mixtures of these. Phosphate, citrate and acetate buffer or mixtures of these are preferably used, especially preferably phosphate/citrate buffers.

In addition to the active ingredient and the buffer, the formulation according to the invention can comprise other physiologically acceptable auxiliaries, for example auxiliaries for adapting tonicity to the tonicity of blood or tissue, for example non-reducing sugars, sugar alcohols such as mannitol, sorbitol, xylitol or glycerin. Moreover, one or more amino acids such as, for example, alanine, arginine, glycine, histidine or/and methionine, may be added to the formulation according to the invention to further increase the chemical stability. Methionine is preferred in this context. The methionine concentration is preferably in the range of 0.1 to 4 mmol/l. A concentration of 2 mmol/l is especially preferred. Moreover, the composition may comprise thickeners for increasing the viscosity, for example for ophthalmological purposes. Examples of suitable thickeners are ophthalmologically suitable polymers, for example Carbopol, methylcellulose, carboxymethylcellulose etc.

Moreover, the composition according to the invention may also comprise preservatives. For ophthalmological purposes, for example, thiomersalate may be employed in an amount of 0.001 to 0.004% (weight/volume).

The invention furthermore relates to pharmaceutical preparations which comprise a liquid interferon-β-comprising formulation as described above. These pharmaceutical preparations are particularly suitable for oral, parenteral or ophthalmological application. The formulations preferably exist in unit doses of 1 to 25 MU IFN-β. The invention furthermore relates to a process for the preparation of such pharmaceutical preparation, in which a formulation according to the invention and, if appropriate, other pharmaceutical formulation auxiliaries which are necessary are prepared and formulated as a suitable dosage form.

The formulation according to the invention can be stored in suitable, washed and sterilized glass vials (hydrolytic class 1) with pharmaceutically acceptable rubber stoppers.

Moreover, formulations according to the invention can also be packaged aseptically in ready-to-use syringes or else in carpules for use in self-injection systems, and employed thus. While this is not preferred, the aqueous solutions may be freeze-dried by addition of other auxiliaries known to the skilled worker, and, after reconstitution, are available in liquid form.

Using suitable preservatives, it is possible to prepare liquid multidose forms and eye-drop solutions and solutions for dropwise oral application.

The auxiliaries additionally required for preparing the relevant dosage forms are known to the skilled worker.

Finally, the invention relates to a process for improving the shelf life of a liquid formulation which comprises human interferon-β as active ingredient and a buffer for setting a pH of 5 to 8, preferably of above 5.5 to 8, characterized in that a formulation without human serum albumin or/and with one or more amino acids is used. The improvement in shelf life encompasses improved long-term stability of the biological activity (in vitro), of the chemical integrity or/and of the physical integrity as indicated hereinabove.

The invention is furthermore illustrated by the examples which follow.

EXAMPLES

An interferon-β obtained from CHO cells was used in all the examples.

1. Long-Term Stability of Liquid Interferon-β Formulations at 25° C.

The following formulations were tested:

Formulation 1: 50 mmol/l sodium citrate pH 5.0

Formulation 2: 50 mmol/l sodium citrate, 50 mmol/l sodium phosphate pH 7.0, 15 mg/ml human serum albumin, 2 mmol/l methionine, 50 mg/ml glycerin Formulation 3: 50 mmol/l sodium citrate, 50 mmol/l sodium phosphate pH 7.0, 50 mg/ml glycerin, 2 mmol/l methionine Formulation 4: 50 mmol/l sodium citrate, 50 mmol/l sodium phosphate pH 7.0, 2 mmol/l methionine Formulation 5: 50 mmol/l sodium citrate, 50 mmol/l sodium phosphate pH 7.0

Formulation 17: 70 mmol/l sodium citrate, 50 mmol/l sodium phosphate, 2 mmol/l methionine, pH 6.5

The formulations were diluted to a content of approx. 10 to 15 MU/ml (that is to say 10 to 15×10⁶ IU/ml).

With the exception of formulation 17 (see below), the formulations were stored at 25° C. for the period indicated in hydrolytic class 1 glass vials (DIN 2R vials) which were sealed with commercially available chlorobutyl rubber stoppers. The biological activity (in vitro) was determined as described by Stewart, W. E. II (1981): The Interferon System (Second, enlarged edition) Springer-Verlag: Vienna, N.Y.; Grossberg, S. E. et al. (1984) Assay of Interferons. In: Came, P. E., Carter W. A. (eds.) Interferons and their Applications, Springer-Verlag: Berlin, Heidelberg, N.Y., Tokyo, pp. 23–43.

The results are shown in Tables 1 to 5. "% (ref.)" indicates the biological activity based on the biological activity of a reference sample which had been stored at −20° C. for the period indicated. "% (Omo)" is the percentage of biological activity based on the initial value at 0 months.

TABLE 1

(Formulation 1):

| | Active ingredient content | | | |
|---|---|---|---|---|
| | MU/ml | | Recovery (25° C.) | |
| Months | −20° C. | 25° C. | % (ref.) | % (0 mo.) |
| 0 | 11.0 | 11.0 | 100 | 100 |
| 1 | 10.0 | 9.8 | 98 | 89 |
| 2 | 9.7 | 11.0 | 113 | 100 |
| 3 | 10.0 | 10.6 | 106 | 96 |
| 4 | 10.3 | 9.5 | 92 | 86 |
| 5 | 9.5 | 9.7 | 102 | 88 |
| 6 | 10.5 | 10.2 | 97 | 93 |

TABLE 2

(Formulation 2):

| | Active ingredient content | | | |
|---|---|---|---|---|
| | MU/ml | | Recovery (25° C.) | |
| Months | −20° C. | 25° C. | % (ref.) | % (0 mo.) |
| 0 | 13.9 | 13.9 | 100 | 100 |
| 1 | 14.0 | 11.9 | 85 | 86 |
| 2 | 13.0 | 11.6 | 89 | 83 |
| 3 | 13.1 | 9.6 | 73 | 69 |
| 4 | 12.5 | 8.8 | 70 | 63 |
| 5 | 11.0 | 8.2 | 75 | 59 |
| 6 | 13.3 | 8.4 | 63 | 60 |

TABLE 3

(Formulation 3):

| | Active ingredient content | | | |
|---|---|---|---|---|
| | MU/ml | | Recovery (25° C.) | |
| Months | −20° C. | 25° C. | % (ref.) | % (0 mo.) |
| 0 | 12.5 | 12.5 | 100 | 100 |
| 1 | 9.4 | 10.0 | 106 | 80 |
| 2 | 8.3 | 11.5 | 139 | 92 |
| 3 | 7.8 | 11.8 | 151 | 94.4 |
| 4 | 6.8 | 10.3 | 151 | 82.4 |
| 5 | 6.6 | 11.2 | 170 | 89.6 |
| 6 | 7.8 | 13.4 | 172 | 107.2 |

TABLE 4

(Formulation 4):

| | Active ingredient content | | | |
|---|---|---|---|---|
| | MU/ml | | Recovery (25° C.) | |
| Months | −20° C. | 25° C. | % (ref.) | % (0 mo.) |
| 0 | 11.4 | 11.4 | 100 | 100 |
| 1 | 10.5 | 10.2 | 97 | 89 |
| 2 | 11.9 | 11.1 | 93 | 97 |
| 3 | 10.8 | 10.0 | 93 | 88 |
| 4 | 10.4 | 9.3 | 89 | 82 |
| 5 | 11.6 | 8.4 | 72 | 74 |
| 6 | 12.4 | 9.5 | 77 | 83 |

TABLE 5

(Formulation 5):

| | Active ingredient content | | | |
|---|---|---|---|---|
| | MU/ml | | Recovery (25° C.) | |
| Months | −20° C. | 25° C. | % (ref.) | % (0 mo.) |
| 0 | 11.3 | 11.3 | 100 | 100 |
| 1 | 11.0 | 9.7 | 88 | 86 |
| 2 | 11.7 | 10.1 | 86 | 89 |
| 3 | 11.1 | 10.2 | 92 | 90 |
| 4 | 11.3 | 10.2 | 90 | 90 |
| 5 | 12.0 | 9.2 | 77 | 81 |
| 6 | 11.0 | 9.7 | 88 | 86 |

It can be seen from the above tables that formulations which do not contain human serum albumin (Formulations 1, 3, 4, 5) surprisingly exhibit a better stability than a formation which comprises human serum albumin (Formulation 2).

In Formulation 17 (see above), an interferon solution with human serum albumin was brought to an activity of 6 MU/0.5 ml under aseptic conditions. The colourless, clear solution was subsequently filter-sterilized, and 0.5-ml aliquots were filled into pre-sterilized disposable syringes and sealed. The ready-to-use syringes were stored at 25° C. and examined for clarity, pH and biological activity. The following results were obtained:

| Storage in months | pH | Clarity [%] | MU/syringe −20° C. | MU/syringe 25° C. | Recovery (25° C.) % (ref.) | Recovery (25° C.) % (0 mo.) |
|---|---|---|---|---|---|---|
| 0 | 6.5 | 99.5 | 6.3 | 6.3 | 100 | 100 |
| 3 | 6.5 | 99.1 | 5.6 | 6.1 | 108 | 97 |

2. Long-Term Stability of Liquid IFN-β Formulations at 37° C.

The following formulations in ready-to-use syringes were tested:

Formulation 6: 50 mmol/l sodium citrate, 50 mmol/l sodium phosphate pH 7.0, 2 mmol/l methionine Formulation 7: 50 mmol/l sodium citrate pH 5.0, 18 mg/ml glycerin, 2 mmol/l methionine Formulation 8: 50 mmol/l sodium citrate pH 5.0, 18 mg/ml glycerin, 15 mg/ml human serum albumin, 2 mmol/l methionine Formulation 9: 50 mmol/l sodium citrate pH 6.0, 18 mg/ml glycerin, 2 mmol/l methionine Formulation 10: 50 mmol/l sodium citrate pH 6.5, 18 mg/ml glycerin, 2 mmol/l methionine The formulations were tested in dosage strengths of 3 MU per 0.5 ml (dosage strength 3), 6 MU per 0.5 ml (dosage strength 6) and 12 MU per ml (dosage strength 12).

The results are shown in Table 6 which follows.

Formulation 12: 50 mmol/l sodium citrate, 50 mmol/l sodium phosphate pH 7.0 to 7.2

Formulation 13: 50 mmol/l sodium citrate, 18 mg/ml glycerin, 2 mmol/l methionine, pH 5.0 to 5.2

Formulation 14: 50 mmol/l sodium citrate, 18 mg/ml glycerin, pH 5.0 to 5.2

Formulation 15: 50 mmol/l sodium citrate, 15 mg/ml human serum albumin (medical grade), 18 mg/ml glycerin, 2 mmol/l methionine, pH 5.0 to 5.2

Formulation 16: 50 mmol/l sodium citrate, 15 mg/ml human serum albumin (medical grade), 18 mg/ml glycerin, pH 5.0 to 5.2 (comparison)

In all batches, the IFN-β content was between 10 and 11 MU/ml.

Testing Procedure

To carry out the analyses, the samples had to be concentrated. Moreover, the human serum albumin had to be removed in the case of batches 15 and 16. This is why the batches were passed over an anti-β chromatography column. The initial volume per batch was 32 ml. Batches 13 to 16 were neutralized prior to anti-β chromatography by addition of 2.1 ml of 0.4 mol/l $Na_2HPO_4$ and 2.1 ml of 0.4 mol/l $Na_3PO_4$.

For the immunoadsorption of interferon-β on a monoclonal antibody against interferon-β (BO2 sepharose 6B, crosslinked by Celltech), a C10 chromatography column (Pharmacia) was packed with 5 ml of BO2 sepharose and washed 3 times with in each case 5–10 gel volumes of PBS, 0.1 mol/l sodium phosphate pH 2.0 and PBS/i mol/l KCl at a linear flow rate of 1.0 cm/min.

Approximately 32 ml of the interferon/HSA-containing solution was applied at a linear flow rate of 0.5 cm/min.

Washing was effected with 10 gel volumes of PBS/1 mol/l KCl with a linear flow rate of 1 cm/min until the OD had dropped to baseline. Elution was done with approximately 1–2 gel volumes of 0.1 mol/l sodium phosphate pH 2.0 at a linear flow rate of 1 cm/min. Interferon-β is obtained as single peak in high purity. This eluate is suitable for the subsequent protein characterization.

TABLE 6

| Storage in months | Dosage strength 3 Formulation | | | | | Dosage strength 6 Formulation | | | | | Dosage strength 12 Formulation | | | | |
|---|---|---|---|---|---|---|---|---|---|---|---|---|---|---|---|
| | 6 | 7 | 8 | 9 | 10 | 6 | 7 | 8 | 9 | 10 | 6 | 7 | 8 | 9 | 10 |
| 0 | 100 | 100 | 100 | 100 | 100 | 100 | 100 | 100 | 100 | 100 | 100 | 100 | 100 | 100 | 100 |
| 1 | 71 | 80 | 61 | 74 | 69 | 72 | 85 | 63 | 86 | 84 | 87 | 88 | 71 | 76 | 84 |
| 2 | 51 | 82 | 33 | 74 | 85 | 61 | 81 | 43 | 80 | 76 | 69 | 88 | 48 | 77 | 81 |
| 3 | 44 | 76 | 23 | 63 | 65 | 48 | 64 | 36 | 73 | 69 | 66 | 72 | 35 | 80 | 81 |
| 4 | 33 | 51 | 16 | 61 | 61 | 46 | 65 | 26 | 84 | — | — | 64 | 24 | 78 | 79 |

The results of Table 6 show that, surprisingly, the formulations according to the invention without human serum albumin exhibit an improved stability at 37° C.

3. Chemical stability at 25° C.

To examine the chemical stability of liquid formulations of IFN-β, 7 batches were formulated and stored at 25° C. After 3 and 6 months, the protein was characterized by means of Lys-C mapping and complete carbohydrate analysis. The formation of methionine sulphoxide and the desialylation was checked particularly carefully.

In addition to Formulation 10 (see above), the following formulations were tested:

Formulation 11: 50 mmol/l sodium citrate, 50 mmol/l sodium phosphate, 2 mmol/l methionine pH 7.0 to 7.2

Analytical Procedure

1. Lys-C Mapping

Using the Achromobacter (AP) enzyme endoproteinase Lys-C, interferon-β is cleaved under reducing conditions on the C-terminal end of lysin to give 12 peptides.

50 µl of eluate from the anti-β chromatography (12.5–50 µg of interferon-β) were placed into an Eppendorf reaction vessel, and 5 µl of 2 mol/l TRIS were added. Wako endoproteinase was added in an enzyme/substrate ratio of 1:10 (endoproteinase Lys-C solution in 50 mmol/l TRIS/HCl, pH 9.0). The solution was mixed and incubated for 2 hours at 30° C. Then, 5 µl of 0.1 mol/l DTT were added to the batch.

The peptides were separated on a reversed-phase column (Vydac C18, 300 Å, 5 µm, 2.1 mm) on an HPLC system HP 1090 M series with diode array detector at 214 mm, for which purpose a gradient of A: 0.1% (v/v) TFA and B: 0.1% (v/v) TFA/70% (v/v) acetonitrile was used. The peptides were numbered consecutively in the sequence of their retention times and are allocated to the following sequences:

| SEQ. ID. No. | Peptide | Position | Sequence |
|---|---|---|---|
| 1 | AP1 | 109–115 | EDFTRGK |
| 2 | AP2 | 100–105 | TVLEEK |
| 3 | AP3 | 46–52 | QLQQFQK |
| 4 | AP4(ox) | 116–123 | LM(ox)SSLHLK |
| 5 | AP4 | 116–123 | LMSSLHLK |
| 6 | AP6(ox) | 35–45 | DRM(ox)NFDIPEEIK |
| 7 | AP5 | 124–134 | RYYGRILHYLK |
| 8 | AP6 | 34–45 | DRMNFDIPEEIK |
| 9 | AP7 | 20–33 | LLWQLNGRLEYCLK |
| 10 | AP8(ox) | 1–19 | M(ox)SYNLLGFLQRSSNFQCQK |
| 11 | AP8 | 1–19 | MSYNLLGFLQRSSNFQCQK |
| 12 | AP9 | 137–166 | EYSHCAWTIVRVEILRNFYFINRLTGYLRN |
| 13 | AP10(ox) | 53–99 | EDAALTIYEM(ox)LQNIFAIFRQDSSSTGWNETIVENLLANVYHQINHLK |
| 14 | AP10 | 53–99 | EDAALTIYEMLQNIFAIFRQDSSSTGWNETIVENLLANVYHQINHLK |

References:

Utsumi et al. (1989). Characterization of four different mammalian-cell-derived recombinant human interferon-β1. Eur. J. Biochem. 181, 545–553.

Utsumi et al. (1988): Structural characterization of fibroblast human interferon-β1. J. Interferon Res. 8, 375–384

Allen, G. (1981): Laboratory techniques in biochemistry and molecular biology. Sequencing of proteins and peptides. Elsevier Verlag.

Castagnola et al. (1988): HPLC in Protein sequence determinations. J. Chromatography 440, 213–251.

In the peptides marked (ox), the amino acid methionine is in the form of methionine sulphoxide. The quantification is based on determining the proportion of the peak area of the oxidized peptide relative to the total area of intact peptide and oxidized peptide. The proportions of oxidized methionines are very low in fresh interferon-β preparations. However, the proportion increases more or less drastically during storage, depending on the storage conditions (buffer, pH, temperature etc.). This change is undesired since it contributes to the instability of the interferon-β molecule or can significantly affect the in-vivo properties.

The proportion of the oxidized peptides AP4(ox), AP6(ox), AP8(ox) and AP10(ox) is thus an important criterion for assessing the chemical integrity of the interferon-β molecule in a liquid formulation.

2. Carbohydrate Determination

In the first step, the oligosaccharides were separated from the polypeptide and demineralized.

Approximately 0.7 ml of the eluate of the anti-β chromatography were dialysed for 16–20 hours at room temperature in a dialysis tubing (diameter 6 mm, Sigma No. D-9277) against 500 ml of dialysis buffer (0.05 mol/l sodium phosphate, 0.10 mol/l NaCl, pH 7.25), with gentle stirring. Then, the tubing was cut open at one end and the contents squeezed into a Eppendorf reaction vessel. After dialysis, the sample volume was 1 ml.

20 μl of Tween 20 (10% strength) and 15 μl of N-glycosidase F solution (Boehringer Mannheim) were pipetted to the dialysed sample. This mixture was incubated for 24 hours at 37° C. After the incubation had ended, the mixture was centrifuged for 10 minutes at 10,000 rpm, filtered through a 0.45 μm filter and subsequently chromatographed and fractioned over a desalting column (HR 10/10 Pharmacia No. 17-0591-01) with an isokratic gradient (eluent A: distilled water) at a flow rate of 1.0 ml/min. The free oligosaccharides were detected at 206 nm.

In the second step, the oligosaccharides which had been liberated were separated by an ion exchanger as a function of the number of the sialic acid residues.

The oligosaccharides contained in the eluate of the desalted column, approx. 2 ml, were bound to an anion exchanger (Mono Q HR 5/5, Pharmacia No. 17-0546-01). The asialo forms are in the eluate. With the aid of a shallow NaCl gradient, monosialo, disialo and trisialo forms eluted distinctly separately one after the other in the sequence indicated.

Eluent A: Milli-Q water
Eluent B: 0.10 mol/l NaCl

| Gradient | | |
|---|---|---|
| 0 min | 100% A | 0% B |
| 5 min | 100% A | 0% B |
| 25 min | 33% A | 67% B |
| 26 min | 100% A | 0% B |

Flow rate: 0.75 ml/min
Chromatography time: 26 min (with regeneration 36 min)
Detection: UV 206 nm The individual oligosaccharide fractions were detected by means of a UV detector at 206 nm. The quantitative calculation was done by integrating the areas of the individual peaks.

The oligosaccharide fractions monosialo, disialo and trisialo were subsequently passed over a desalting column as described above.

In the third step, the charged oligosaccharides are converted into neutral oligosaccharides by hydrolytically eliminating the terminal sialic acid residues under acidic pH conditions.

To this end, approx. 15 μl of each oligosaccharide fraction plus 15 μl of Milli Q water were placed into a micro-test tube, and 30 μl of 10 mmol/l $H_2SO_4$ were added. The mixture was then heated for 90 minutes at 80° C.

Then, the batch was centrifuged for 1 minute at 5000 rpm and pipetted into a minivial. The carbohydrates, which are now neutral, are bound at alkaline pH to weak anions and on an anion-exchanger column (CarboPac PA1 (4×250 mm) P/N 35391, Dionex) Elution is done with a gradient of Eluent A: NaOH 0.16 mol/l
Eluent B: NaOH 0.16 mol/l sodium acetate 0.10 mol/l
Eluent C: NaOH 0.16 mol/l sodium acetate 0.75 mol/l
Gradient:

| 0 min | 95% A | 5% B | 0% C |
|---|---|---|---|
| 2.0 min | 95% A | 5% B | 0% C |
| 3.0 min | 85% A | 15% B | 0% C |
| 4.0 min | 85% A | 15% B | 0% C |
| 28.0 min | 37% A | 63% B | 0% C |
| 28.1 min | 90% A | 0% B | 10% C |

-continued

| | | | |
|---|---|---|---|
| 45.0 min | 20% A | 0% B | 80% C |
| 45.1 min | 95% A | 5% B | 0% C |
| 50.0 min | 95% A | 5% B | 0% C |

Flow rate: 1.0 ml/min
Chromatography time: 50 min
Detection: PAD

PAD (pulsed amperometric detection) was used to determine the oligosaccharides. The oligosaccharide molecule is electrochemically oxidized, and the current thus formed measured. PAD is distinguished by a high sensitivity, so that a detection in the ng range presents no difficulty. The output signal in the detector (in mV) is directly proportional to the amount of carbohydrate. Quantification is done by integrating the peak areas.

Between the deglycosylation and the analysis, the samples were subjected to intermediate storage at −20° C.

References:
Townsend (1988): High-performance anion-exchange chromatography of oligosaccharides. Analytical Biochemistry 174, 459–470.

Results

1. Lys-C Mapping

The Lys-C mapping of batches 11 to 16 showed no difference to the initial value with regard to retention time and qualitative determination of the peptides.

The determination of the methionine sulphoxide content during liquid storage revealed the results shown in Tables 7 (3 months' storage) and 8 (6 months' storage).

TABLE 7

| Name | AP4ox content | AP6ox content | AP8ox content | AP10ox content |
|---|---|---|---|---|
| to value | <5% | 7.6% | n.d. | n.d. |
| Formulation 11 | 7.9% | 10.5% | n.d. | n.d. |
| Formulation 12 | <5% | 11.6% | n.d. | n.d. |
| Formulation 13 | <5% | 7.3% | n.d. | n.d. |
| Formulation 14 | <5% | 9.4% | n.d. | n.d. |
| Formulation 15 | <5% | 8.6% | n.d. | n.d. |
| Formulation 16 | <5% | 10.8% | n.d. | n.d. |

(n.d. = not detectable)

TABLE 8

| Name | AP4ox content | AP6ox content | AP8ox content | AP10ox content |
|---|---|---|---|---|
| to value | <5% | 7.6% | n.d. | n.d. |
| Formulation 10 | 7.6% | 8.9% | n.d. | n.d. |
| Formulation 11 | 7.7% | 9.5% | n.d. | n.d. |
| Formulation 12 | 12.0% | 13.7% | n.d. | n.d. |
| Formulation 13 | 7.4% | 8.7% | n.d. | n.d. |
| Formulation 14 | 13.7% | 15.7% | n.d. | n.d. |
| Formulation 15 | 7.4% | 7.9% | n.d. | n.d. |
| Formulation 16 | 18.0% | 17.6% | n.d. | n.d. |

Table 7 reveals that the methionine-containing batches 13 and 15 show a lower methionine sulphoxide content upon three months' storage in comparison with methionine-free batches. After storage for six months, the affect of the added methionine in batches 11, 13 and 15 is more pronounced. Only a very small increase in the methionine sulphoxide content can be detected in these batches. In the methionine-free batches, the methionine sulphoxide content increases slightly more, but the total of all oxidized methionine contents amounts to less than 10% of the total methionine content.

2. Carbohydrate Determination

The results of the carbohydrate determination after storage for three or 6 months are shown in Tables 9a, 9b, 10a, 10b, 11a and 11b.

Interferon-β 1a has a carbohydrate structure on its amino acid chain which is composed of a defined sequence of monosaccharides. Depending on the type of branching, these structures are termed biantennary (2 arms), triantennary (3 arms) and tetraantennary (4 arms).

The carbohydrate structure is composed of the monosaccharides mannose, fucose, N-acetylglucosamine, galactose and sialic acid.

In this context, the sialic acid is special in several respects:

It is the only monosaccharide with a charged group (carboxyl group).

It always occurs at the terminus of the carbohydrate chain.

It can be eliminated enzymatically or hydrolytically considerably more readily than the remaining monosaccharides.

While the structure of the neutral carbohydate chain is highly constant, the sialic acid moiety varies greatly depending, inter alia, on the cell culture and the purification method of the interferon.

References:
Kagawa et al., J. Biol. Chem. 263 (1988), 17508–17515; EP-A-0 529 300.

The sialostatus (percentage of individual sialo structures) after three months' storage (Table 9a) or six months' storage (Table 9b) was investigated. A carbohydrate structure which does not contain a terminal sialic acid is termed asialo. A carbohydrate structure which contains a terminal sialic acid is termed monosialo. A carbohydrate structure which contains two terminal sialic acids is termed disialo. A carbohydrate structure which contains three terminal sialic acids is termed trisialo.

Furthermore, the antennarity (percentage of individual branching types) was determined after three months' storage (Table 10a) and after six months' storage (Table 10b). A carbohydrate structure with one branching and thus two terminal galactoses is termed biantennary. It can have zero to two terminal sialic acids. A carbohydrate structure with two branchings and thus three terminal galactoses is termed triantennary. It can have zero to three terminal sialic acids.

The degree of sialylation (percentage occupation of terminal galactose residues with sialic acid) after three months' storage (Table 11a) and six months' storage (Table 11b) was also investigated.

It can be seen from the results that storage at pH 5 causes a slight, but reproducible, desialylation. Storage at pH 7 has no effect on the degree of sialylation.

The afuco content specified in batches 15 and 16 is probably due to foreign proteins from the added human serum albumin, which were not quantitatively removed by anti-β chromatography.

As regards the antennarity, liquid storage has no measureable effect.

TABLE 9a

| Name | Asialo | Monoasialo | Disialo | Trisialo |
|---|---|---|---|---|
| to value | <3 | 13.4 | 73.4 | 12.1 |
| Formulation 11 | <3 | 14.0 | 74.1 | 11.9 |
| Formulation 12 | <3 | 12.6 | 74.9 | 11.6 |
| Formulation 13 | <3 | 16.5 | 70.4 | 12.0 |
| Formulation 14 | <3 | 16.6 | 71.1 | 11.1 |
| Formulation 15 | <3 | 15.8 | 70.0 | 13.0 |
| Formulation 16 | <3 | 15.1 | 72.0 | 11.9 |

TABLE 9b

| Name | Asialo | Monoasialo | Disialo | Trisialo |
|---|---|---|---|---|
| to value | <3 | 13.4 | 73.4 | 12.1 |
| Formulation 10 | <3 | 13.9 | 70.2 | 15.3 |
| Formulation 11 | <3 | 14.5 | 73.9 | 11.6 |
| Formulation 12 | <3 | 14.0 | 72.4 | 13.6 |
| Formulation 13 | <3 | 18.6 | 68.9 | 11.7 |
| Formulation 14 | <3 | 19.0 | 69.4 | 10.7 |
| Formulation 15 | <3 | 17.0 | 71.0 | 11.3 |
| Formulation 16 | <3 | 16.1 | 71.5 | 12.4 |

TABLE 10a

| Name | Biantennary | Triantennary 1→6 | Triantennary + 1 repeat |
|---|---|---|---|
| to value | 74.4 | 18.1 | 3.7 |
| Formulation 11 | 72.9 | 18.7 | 3.7 |
| Formulation 12 | 76.9 | 17.0 | 2.7 |
| Formulation 13 | 74.7 | 18.0 | 3.1 |
| Formulation 14 | 75.9 | 17.3 | 2.9 |
| Formulation 15 | 76.2 (incl. 5% afuco) | 18.0 | 3.3 |
| Formulation 16 | 76.9 (incl. 5% afuco) | 17.8 | 3.0 |

TABLE 10b

| Name | Biantennary | Triantennary 1→6 | Triantennary + 1 repeat |
|---|---|---|---|
| to value | 74.4 | 18.1 | 3.7 |
| Formulation 10 | 71.4 | 19.3 | 4.0 |
| Formulation 11 | 73.0 | 18.7 | 3.3 |
| Formulation 12 | 72.3 | 19.7 | 3.4 |
| Formulation 13 | 72.4 | 19.2 | 3.4 |
| Formulation 14 | 74.2 | 18.7 | 3.2 |
| Formulation 15 | 73.0 | 18.7 | 2.8 |
| Formulation 16 | 74.3 (incl. 4% afuco) | 19.7 | 3.2 |

TABLE 11a

| Name | Degree of sialylation |
|---|---|
| to value | 88.3 |
| Formulation 11 | 87.0 |
| Formulation 12 | 88.2 |
| Formulation 13 | 85.8 |
| Formulation 14 | 85.8 |
| Formulation 15 | 86.6 |
| Formulation 16 | 86.9 |

TABLE 11b

| Name | Degree of sialylation |
|---|---|
| to value | 88.3 |
| Formulation 10 | 87.5 |
| Formulation 11 | 86.6 |
| Formulation 12 | 87.7 |
| Formulation 13 | 84.1 |
| Formulation 14 | 84.3 |
| Formulation 15 | 85.7 |
| Formulation 16 | 86.5 |

What is claimed is:

1. A liquid formulation comprising a glycosylated human interferon-β as an active ingredient, a buffer which buffers in a pH range of 5 to 8, and methionine present in a concentration of 0.1 to 4 mmol/l, with the proviso that the formulation does not contain human serum albumin, and wherein after storage for 3 months at 25° C., stability of an in vitro biological activity of the formulation is at least 80% of an initial biological activity, wherein said biological activity comprises inhibition of a cytopathic effect of a virus.

2. The formulation according to claim 1, wherein the pH is between 6 and 7.2.

3. The formulation according to claim 1, wherein the formulation, apart from the active ingredient, is free from animal polypeptides.

4. The formulation according to claim 1, wherein the formula is free from surfactants.

5. The formulation according to claim 1, wherein after storage of the formulation for 6 months at 25° C., the formulation is chemically stable.

6. The formulation according to claim 1, wherein after storage of the formulation for 6 months at 25° C., the formulation is physically stable.

7. The formulation according to claim 1, further comprising an ingredient for adjusting tonicity.

8. The formulation according to claim 1, comprising a thickener for increasing viscosity.

9. The formulation according to claim 1, further containing at least one physiologically acceptable preservative.

10. A pharmaceutical composition comprising a liquid formulation according to claim 1, and a pharmaceutically acceptable carrier.

11. The pharmaceutical composition according to claim 10, in a form suitable for oral, parenteral or ophthalmological administration.

12. The pharmaceutical composition according to claim 10, wherein the composition is in the form of a unit containing 1 to $25 \times 10^6$ IU of interferonon-β.

13. A liquid formulation consisting of human interferon-β, 70 mmol/L sodium citrate, 50 mmol/L sodium phosphate, and 2 mmol/L methionine, having a pH in a range of about 6.2 to about 6.8.

14. The liquid formulation of claim 13, wherein the formulation has a pH of about 6.5.

15. The liquid formulation of claim 1, wherein the methionine is present in a concentration of 2 mmol/l.

16. A method for increasing the long-term stability, including the in vitro biological activity stability, of a liquid formulation comprising human interferon-β as an active ingredient, said method comprising adding a buffer for buffering in a pH range of 5 to 8, while avoiding the presence of human serum albumin in the formulation, and adding a stabilizing amount of methionine to the formulation, wherein the stabilizing amount of methionine is a concentration of methionine that is 0.1 to 4 mmol/l.

17. The method of claim 16, wherein the stabilizing amount of methionine is a concentration of methionine that is 2 mmol/l.

18. The formulation of claim 13, wherein the human interferon-β has a concentration of about $10 \times 10^6$ IU/ml to about $15 \times 10^6$ IU/ml.

19. The formulation of claim 18, wherein the human interferon-β has a concentration of about $12 \times 10^6$ IU/ml.

\* \* \* \* \*

SEQUENCE LISTING

<160> NUMBER OF SEQ ID NOS: 14

<210> SEQ ID NO 1
<211> LENGTH: 7
<212> TYPE: PRT
<213> ORGANISM: Homo sapiens

<400> SEQUENCE: 1

Glu Asp Phe Thr Arg Gly Lys
1               5

<210> SEQ ID NO 2
<211> LENGTH: 6
<212> TYPE: PRT
<213> ORGANISM: Homo sapiens

<400> SEQUENCE: 2

Thr Val Leu Glu Glu Lys
1               5

<210> SEQ ID NO 3
<211> LENGTH: 7
<212> TYPE: PRT
<213> ORGANISM: Homo sapiens

```
<400> SEQUENCE: 3

Gln Leu Gln Gln Phe Gln Lys
1               5

<210> SEQ ID NO 4
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: "X" = any amino acid

<400> SEQUENCE: 4

Leu Xaa Ser Ser Leu His Leu Lys
1               5

<210> SEQ ID NO 5
<211> LENGTH: 8
<212> TYPE: PRT
<213> ORGANISM: Homo sapiens

<400> SEQUENCE: 5

Leu Met Ser Ser Leu His Leu Lys
1               5

<210> SEQ ID NO 6
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: "X" = any amino acid

<400> SEQUENCE: 6

Asp Arg Xaa Asn Phe Asp Ile Pro Glu Glu Ile Lys
1               5                   10

<210> SEQ ID NO 7
<211> LENGTH: 11
<212> TYPE: PRT
<213> ORGANISM: Homo sapiens

<400> SEQUENCE: 7

Arg Tyr Tyr Gly Arg Ile Leu His Tyr Leu Lys
1               5                   10

<210> SEQ ID NO 8
<211> LENGTH: 12
<212> TYPE: PRT
<213> ORGANISM: Homo sapiens

<400> SEQUENCE: 8

Asp Arg Met Asn Phe Asp Ile Pro Glu Glu Ile Lys
1               5                   10

<210> SEQ ID NO 9
<211> LENGTH: 14
<212> TYPE: PRT
<213> ORGANISM: Homo sapiens

<400> SEQUENCE: 9

Leu Leu Trp Gln Leu Asn Gly Arg Leu Glu Tyr Cys Leu Lys
1               5                   10
```

```
<210> SEQ ID NO 10
<211> LENGTH: 19
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: "X" = any amino acid

<400> SEQUENCE: 10

Xaa Ser Tyr Asn Leu Leu Gly Phe Leu Gln Arg Ser Ser Asn Phe Gln
1               5                   10                  15

Cys Gln Lys

<210> SEQ ID NO 11
<211> LENGTH: 19
<212> TYPE: PRT
<213> ORGANISM: Homo sapiens

<400> SEQUENCE: 11

Met Ser Tyr Asn Leu Leu Gly Phe Leu Gln Arg Ser Ser Asn Phe Gln
1               5                   10                  15

Cys Gln Lys

<210> SEQ ID NO 12
<211> LENGTH: 30
<212> TYPE: PRT
<213> ORGANISM: Homo sapiens

<400> SEQUENCE: 12

Glu Tyr Ser His Cys Ala Trp Thr Ile Val Arg Val Glu Ile Leu Arg
1               5                   10                  15

Asn Phe Tyr Phe Ile Asn Arg Leu Thr Gly Tyr Leu Arg Asn
                20                  25                  30

<210> SEQ ID NO 13
<211> LENGTH: 47
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: "X" = any amino acid

<400> SEQUENCE: 13

Glu Asp Ala Ala Leu Thr Ile Tyr Glu Xaa Leu Gln Asn Ile Phe Ala
1               5                   10                  15

Ile Phe Arg Gln Asp Ser Ser Ser Thr Gly Trp Asn Glu Thr Ile Val
                20                  25                  30

Glu Asn Leu Leu Ala Asn Val Tyr His Gln Ile Asn His Leu Lys
            35                  40                  45

<210> SEQ ID NO 14
<211> LENGTH: 47
<212> TYPE: PRT
<213> ORGANISM: Homo sapiens

<400> SEQUENCE: 14

Glu Asp Ala Ala Leu Thr Ile Tyr Glu Met Leu Gln Asn Ile Phe Ala
1               5                   10                  15
```

```
-continued

Ile Phe Arg Gln Asp Ser Ser Thr Gly Trp Asn Glu Thr Ile Val
            20              25              30

Glu Asn Leu Leu Ala Asn Val Tyr His Gln Ile Asn His Leu Lys
        35              40              45
```